United States Patent [19]

Roth et al.

[11] Patent Number: 4,908,423

[45] Date of Patent: Mar. 13, 1990

[54] ADVANCED EPOXIDE RESINS BASED ON CYCLOHEX-1-YLMETHYLENEDIPHENOL DERIVATIVES OR BICYCLO[2.2.1]HEPT-1-YLMETHYLENEDIPHENOL DERIVATIVES

[75] Inventors: Martin Roth, Giffers; Charles E. Monnier, Villars-sur-Glâne, both of Switzerland

[73] Assignee: Ciba-Geigy Corporation, Ardsley, N.Y.

[21] Appl. No.: 270,995

[22] Filed: Nov. 14, 1988

Related U.S. Application Data

[62] Division of Ser. No. 147,389, Jan. 25, 1988, Pat. No. 4,808,740.

[30] Foreign Application Priority Data

Jan. 30, 1987 [CH] Switzerland .............................. 352/87

[51] Int. Cl.⁴ ............................................. C08G 59/62
[52] U.S. Cl. ..................................... 528/97; 525/523; 525/502; 528/104; 528/101
[58] Field of Search ................... 568/719, 721; 528/97, 528/101, 104; 525/523, 502

[56] References Cited

U.S. PATENT DOCUMENTS

| | | | |
|---|---|---|---|
| 2,775,620 | 12/1956 | Williamson | 568/721 X |
| 3,220,977 | 11/1965 | Jackson et al. | 568/721 X |
| 3,355,414 | 11/1967 | Caldwell et al. | 568/719 X |
| 3,446,855 | 5/1969 | Jackson et al. | 568/721 |
| 3,517,071 | 6/1970 | Caldwell et al. | 568/719 |

*Primary Examiner*—Earl Nielsen
*Attorney, Agent, or Firm*—Luther A. R. Hall

[57] ABSTRACT

The invention relates to compounds of the formula I or II

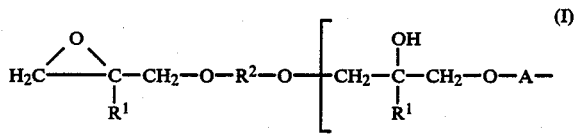

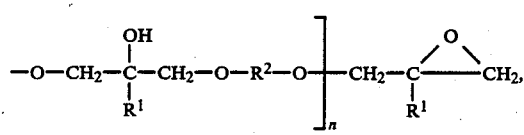

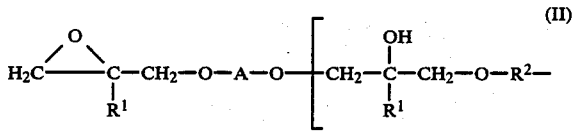

-continued

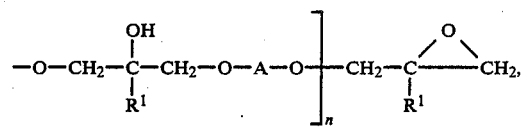

in which A is a radical

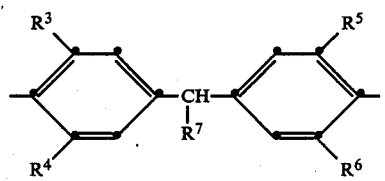

$R^1$ is hydrogen or methyl, $R^2$ is the radical of an aliphatic, cycloaliphatic, aromatic or araliphatic diol after both of the hydroxyl groups have been removed, $R^3$, $R^4$, $R^5$ and $R^6$ independently of one another are hydrogen, $C_1$–$C_6$alkyl, chlorine or bromine, $R^7$ is a radical of the formula III, IV, V or VI

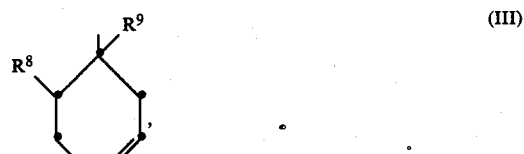 (III)

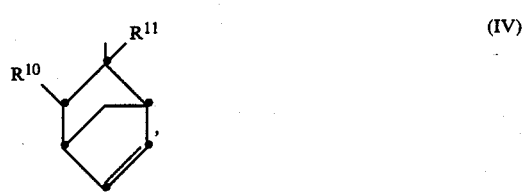

(IV)

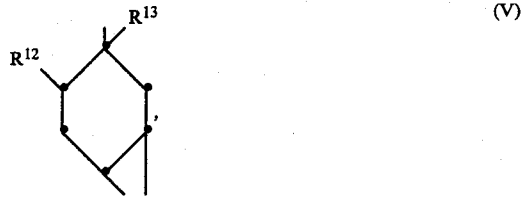

(V)

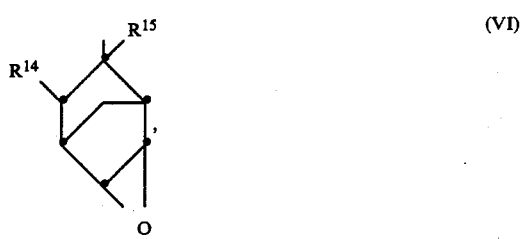

(VI)

$R^8$, $R^{10}$, $R^{12}$ and $R^{14}$ are hydrogen, $C_1$–$C_6$alkyl or phenyl, $R^9$, $R^{11}$, $R^{13}$ and $R^{15}$ are hydrogen or $C_1$–$C_6$al- (Abstract continued on next page.)

kyl and the average value of n (number average) is a number from 1 to 20, it being possible for the radicals $R^1$ to $R^{15}$, within a given molecule, to assume different meanings within the scope of the definitions given.

These compounds or also the epoxidized intermediates of the formula X

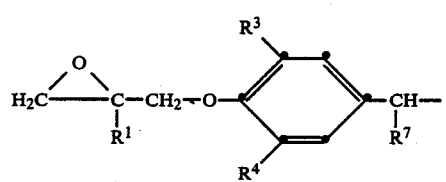 (X)

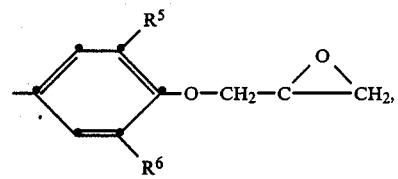

in which $R^1$ to $R^3$ are as defined above and $R^7$ is a radical of the formula IV or VI can be processed to give cured products having a high glass transition temperature and a low tendency to discoloration.

1 Claim, No Drawings

ADVANCED EPOXIDE RESINS BASED ON CYCLOHEX-1-YLMETHYLENEDIPHENOL DERIVATIVES OR BICYCLO[2.2.1]HEPT-1-YLMETHYLENEDI-PHENOL DERIVATIVES

This is a divisional of application Ser. No. 147,389, filed Jan. 25, 1988, now U.S. Pat. No. 4,808,740, issued on Feb. 28, 1989.

The present invention relates to so-called advanced epoxide resins derived from special diphenols or from diglycidyl ethers based on these phenols, to a process for the preparation of the special diphenols, to the novel glycidyl ether intermediates and to curable mixtures containing the so-called advanced derivatives and/or the intermediates in combination with curing agents.

Cyclohex-1-ylmethylenediphenols are known from British Pat. No. 1,024,012. Bicyclo[2.2.1]hept-1-ylmethylenediphenols are described in British Pat. No. 1,024,013. These compounds are employed, for example, as monomer components in the preparation of polycarbonates. Reactions of this type are described in British Pat. No. 1,024,011. The preparation of glycidyl ethers of hydroxylaryl-3,4-epoxycyclohexylmethanes is described by B. M. Tkatschuk et al. (cf. Ref. Zh. Khim., 1985, Abstr. No. 19S419). The compounds prepared in this reference are low-molecular and accordingly have a relatively low viscosity.

For certain applications, for example laminates, oligomers having a more highly built-up structure are advantageous.

A class of so-called advanced epoxide resins which are distinguished by advantageous properties, compared with conventional so-called advanced epoxide resins based on bisphenol A, have now been found.

Thus the cured products from these novel resins as a rule have high glass transition temperatures; in addition products having only a slight discoloration are obtained when they are cured with imidazole accelerators.

The present invention relates to compounds of the formula I or II

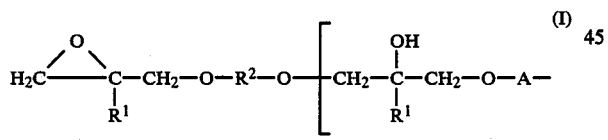

(I)

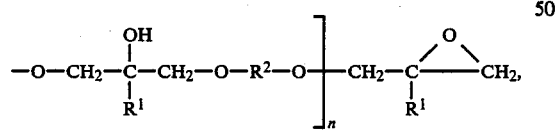

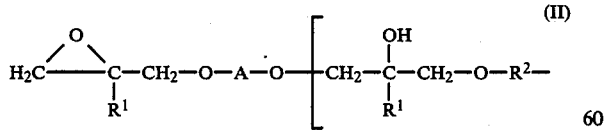

(II)

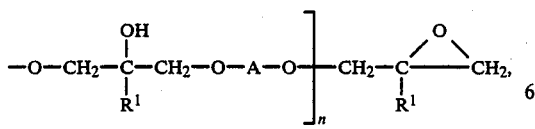

in which A is a radical,

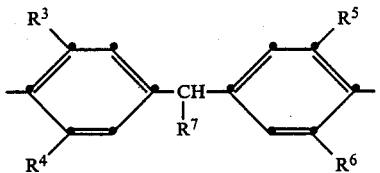

$R^1$ is hydrogen or methyl, $R^2$ is the radical of an aliphatic, cycloaliphatic, aromatic or araliphatic diol after both of the hydroxyl groups have been removed, $R^3$, $R^4$, $R^5$ and $R^6$ independently of one another are hydrogen, $C_1$–$C_6$alkyl, chlorine or bromine, $R^7$ is a radical of the formula III, IV, V or VI

(III)

(IV)

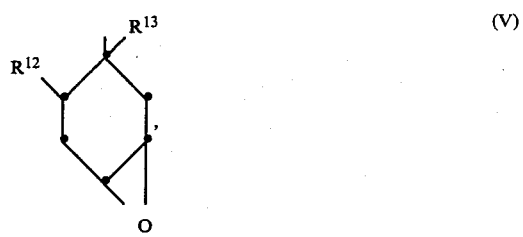

(V)

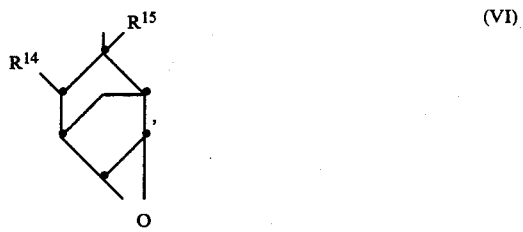

(VI)

$R^8$, $R^{10}$, $R^{12}$ and $R^{14}$ are hydrogen, $C_1$–$C_6$alkyl or phenyl, $R^9$, $R^{11}$ $R^{13}$ and $R^{15}$ are hydrogen or $C_1$–$C_6$alkyl and the average value of n (number average) is a number from 1 to 20, it being possible for the radicals $R^1$ to $R^{15}$, within a given molecule, to assume different meanings within the scope of the definitions given. $R^1$ is preferably hydrogen.

If $R^2$ is derived from an aliphatic diol, it is a linear or branched-chain alkylene radical which can, if desired, be interrupted by oxygen or sulfur atoms and which can be substituted or unsubstituted.

Examples of substituents are chlorine and bromine.

Unsubstituted linear $C_2$–$C_{20}$alkylene radicals are preferred. Examples of these are ethylene, trimethylene, tetramethylene, pentamethylene, hexamethylene, heptamethylene, octamethylene, decamethylene, dodecamethylene, tetradecamethylene, hexadecamethylene, octadecamethylene or eicosamethylene.

Tetramethylene is particularly preferred.

The diol on which $R^2$ is based can, however, also be a poly-(oxyalkylene) glycol or a poly-(thioalkylene) glycol. The derivatives containing oxygen are preferred.

Examples of these are poly-(ethylene) glycol, poly-(propylene) glycol or poly-(butylene) glycol having 2-60 monomer units.

If $R^2$ is derived from a cycloaliphatic diol, it is, for example, a diol having a cycloaliphatic ring containing 5-7 carbon atoms which can, if appropriate, be part of an aliphatic chain or which can, if appropriate, carry substituents directly attached to the ring.

Examples of such radicals are cyclopentylene, cyclohexylene or cycloheptylene.

Cyclohexylene, particularly 1,3-cyclohexylene or 1,4-cyclohexylene, is particularly preferred. Hexahydroxylylene is also of interest.

If $R^2$ is based on an aromatic diol, this radical is preferably derived from a mononuclear or dinuclear phenol. Preferred examples of these are 1,2-phenylene or, in particular, 1,3-phenylene or 1,4-phenylene and also radicals of the formula VII

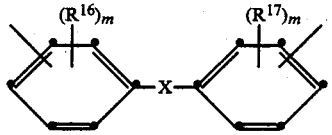

in which the free bonds are preferably in the 3-position or 4-position relative to the bridge X, and X is a direct C—C bond or is selected from the group of radicals consisting of —$CH_2$—, —$CHCH_3$—, —$C(CH_3)_2$, —O—, —S—, —$SO_2$— or —CO—, m is an integer from 0 to 4, preferably 0, 1 or 2 and very particularly preferably 0, and $R^{16}$ and $R^{17}$ independently of one another are $C_1$-$C_6$alkyl, chlorine or bromine.

Preferred radicals $R^2$ are diphenylmethane-4,4'-diyl, diphenylether-4,4'-diyl, diphenylsulfone-4,4'-diyl and, very particularly, diphenyl-2,2-propylidene-4,4'-diyl. Xylylene is an example of $R^2$ as an araliphatic radical.

$C_1$-$C_6$alkyl radicals $R^3$ to $R^6$ and $R^8$ to $R^{17}$ can be linear or branched. Examples of these are methyl, ethyl, n-propyl, isopropyl, n-butyl, sec-butyl, tert-butyl, n-pentyl, or n-hexyl.

Linear $C_1$-$C_4$alkyl radicals, in particular methyl, are preferred.

Compounds of the formula I or II which are very particularly preferred are those in which $R^2$ is a radical of the formula VIIa

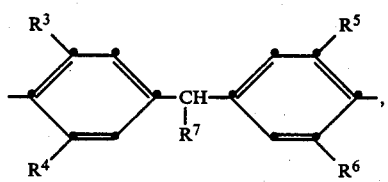

and $R^3$, $R^4$, $R^5$, $R^6$ and $R^7$ are as defined earlier in the text.

The radicals $R^3$ to $R^6$ and $R^8$ to $R^{15}$ are particularly preferably hydrogen.

The compounds of the formula I or II are present, as a rule, as a mixture of components of varying chain length. The average molecular weight (number average; determined by gel permeation chromatography) is at least as high as the molecular weight of the corresponding pure compound in which n is 1.

The average value of n is preferably a number from 1 to 10, very particularly from 1 to 5.

$R^7$ is preferably a radical of the formula III or of the formula IV. Further preferred radicals $R^7$ are the epoxidized types of the formula VI or especially V, in which $R^{12}$, $R^{13}$, $R^{14}$ and $R^{15}$ are hydrogen.

The compounds of the formula I are derived from diphenols of the formula VIII

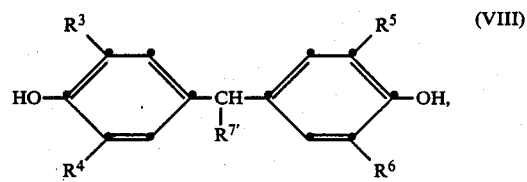

in which $R^3$, $R^4$, $R^5$ and $R^6$ are as defined earlier in the text and $R^{7'}$ is a radical of the formula III or IV. These compounds are known from the British Pat. Nos. 1,024,012 or 1,024,013 mentioned above or can be prepared analogously to the procedures described therein.

The invention also relates, however, to a process for the preparation of compounds of the formula VIII wherein high yields are achieved. This process embraces the reaction of an aldehyde of the formula VIIIa

$$R^{7'}-CHO \quad \text{(VIIIa)},$$

in which $R^{7'}$ is as defined above, with a 4-molar to 8-molar excess, relative to the aldehyde, of a phenol of the formula VIIIb or of a mixture of these phenols

in which $R^a$ and $R^b$ are as defined earlier in the text for $R^3$, $R^4$, $R^5$ and $R^6$; the process comprises the use of a mononuclear aromatic hydrocarbon as the solvent and of an aromatic sulfonic acid as the catalyst. If desired, a mercapto compound can also be present in addition, for example thiolactic acid, mercaptoacetic acid or mercaptopropionic acid. A further increase in the yield can be achieved by this means.

As a rule, the reaction temperature is between −10° C. and the boiling point of the particular solvent (mixture), preferably between 0°-70° C.

Examples of suitable mononuclear aromatic hydrocarbons are benzene, toluene, ethylbenzene, cumene, xylene or chlorobenzene, particularly toluene. It is also possible to employ mixtures.

Examples of suitable aromatic sulfonic acids are benzenesulfonic, toluenesulfonic or naphthalenesulfonic acids, but particularly toluenesulfonic acid. It is also possible to employ mixtures.

The diphenols of the formula VIII in which $R^{7'}$ is, in addition, a radical of the formula V or VI can also be employed as curing agents for curable epoxide resins, which is also a subject of the present invention.

The compounds of the formula I containing the unsaturated radicals R⁷ of the formula III or IV can be obtained in a manner known per se by reacting n moles of a diphenol of the formula VIII with n+1 moles of a diepoxide of the formula IX

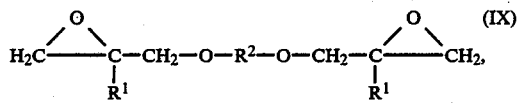

in which n, R1 and R2 are as defined earlier in the text.

The compounds of the formula I containing the epoxidized radicals R⁷ of the formula V or VI can be obtained by epoxidizing a compound of the formula I containing unsaturated radicals R⁷ of the formula III or IV by means of a peracid in a manner known per se.

The epoxidation by means of a peracid can also be carried out in such a way that only part of the unsaturated radicals of the formula III or IV is converted into the corresponding epoxide compound.

The compounds of the formula II are derived from diglycidyl ethers of the formula X

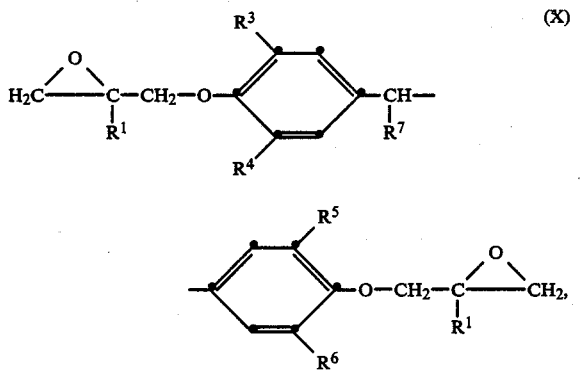

in which R¹, R³, R⁴, R⁵, R⁶ and R⁷ are as defined earlier in the text. These compounds are, therefore, diepoxide or triepoxide compounds, depending the nature of the radical R⁷.

The compounds of the formula X containing the radicals R⁷ of the formulae IV and VI are novel and also form a subject of the present invention.

The diepoxide compounds of the formula X can be obtained from the diphenols of the formula VIII in a manner known per se by reacting the latter with epichlorohydrin or with β-methylepichlorohydrin.

The triepoxide compounds of the formula X can be obtained by reacting the diglycidyl ethers of the formula X, containing unsaturated radicals R⁷ of the formula III or IV with a peracid.

The compounds of the formula II containing unsaturated radicals R⁷ of the formula III or IV can be obtained in a manner known per se by reacting n moles of a diol of the formula XI

in which n and R² are as defined earlier in the text with n+1 moles of a diglycidyl ether of the formula X containing the radicals R⁷ of the formula III or IV.

The compounds of the formula II containing the epoxidized radicals R⁷ of the formula V or VI can be obtained (a) by reacting n+1 moles of the diglycidyl ether of the formula X in which the R⁷s are radicals of the formula V or VI with n moles of a diol of the formula XI in a manner known per se or (b) by epoxidizing a compound of the formula II containing unsaturated radicals R⁷ of the formula III or IV in a manner known per se by means of a peracid.

The epoxidation by means of a peracid can also be carried out in such a way that only a part of the unsaturated radicals of the formula III or IV is converted into the corresponding epoxide compounds.

It is preferable to react n+1 moles of the diglycidyl ether of the formula X with n moles of the diphenol of the formula VIII and, if appropriate, to epoxidize the product with a peracid.

In a further preferred embodiment of the process, n+1 moles of the diphenol of the formula VIII are reacted with n moles of the diglycidyl ether of the formula X and the product, if appropriate, is epoxidized by means of a peracid.

The so-called advancement of the diglycidyl ether IX with the diphenol VIII or of the diglycidyl ether X with the diol XI is carried out analogously to known processes. So-called advancements of this type are carried out in industry, for example in the synthesis of long-chain diglycidyl ethers based on bisphenol, and are described in the "Epoxy Handbook" by Lee and Neville, chapters 2-9.

The epoxidation of olefinically unsaturated compounds by means of peracids is also known and is described, for example, in the "Epoxy Handbook" by Lee and Neville, chapter 3.

The so-called advanced compounds of the formula I or II and also the monomeric starting materials for the so-called advancement reaction of the formula X can be employed in combination with curing agents as curable mixtures.

The invention therefore also relates to a curable mixture containing (a) at least one compound of the formula I or II, (b) an amount of an epoxide curing agent adequate for curing the said mixture, and (c) if appropriate, a curing accelerator.

The invention also relates to a curable mixture containing (a) at least one compound of the formula X in which R⁷ is a radical of the formula IV or VI, (b) an amount of an epoxide curing agent adequate for curing the said mixture, and (c) if appropriate, a curing accelerator.

It is also possible, of course, to employ mixtures of the compounds I, II and/or X, or to use these compounds in combination with other known epoxide resins.

The following should be mentioned as examples of additional epoxide resins which can be employed together with the compounds I, II and/or X:

(I) Polyglycidyl and poly-(β-methyglycidyl) esters which can be obtained by reacting a compound containing at least two carboxyl groups in the molecule and epichlorohydrin or glycerol dichlorohydrin or β-methylepichlorohydrin. The reaction is advantageously carried out in the presence of bases.

Aliphatic polycarboxylic acids can be used as the compound containing at least two carboxyl groups in the molecule. Examples of these polycarboxylic acids are oxalic acid, succinic acid, glutaric acid, adipic acid, pimelic acid, suberic acid, azelaic acid, sebacic acid or dimerized or trimerized linoleic acid.

It is also possible, however, to employ cycloaliphatic polycarboxylic acids, for example tetrahydrophthalic acid, 4-methyltetrahydrophthalic acid, hexahydrophthalic acid or 4-methylhexahydrophthalic acid.

It is also possible to use aromatic polycarboxylic acids, for example phthalic acid, isophthalic acid or terephthalic acid.

(II) Polyglycidyl or poly-($\beta$-methylglycidyl) ethers which can be obtained by reacting a compound containing at least two free alcoholic hydroxyl groups and/or phenolic hydroxyl groups and a suitably substituted epichlorohydrin under alkali conditions, or in the presence of an acid catalyst, with subsequent alkali treatment.

Ethers of this type are derived, for example, from acyclic alcohols, such as ethylene glycol, diethylene glycol and higher poly-(oxyethylene) glycols, propane-1,2-diol or poly-(oxypropylene) glycols, propane-1,3-diol, butane-1,4-diol, poly-(oxytetramethylene) glycols, pentane-1,5-diol, hexane-1,6-diol, hexane-2,4,6-triol, glycerol, 1,1,1-trimethylolpropane, pentaerythritol, sorbitol and also from polyepichlorohydrins.

They are, however, also derived, for example, from cycloaliphatic alcohols, such as 1,3-dihydroxycyclohexane, 1,4-dihydroxycyclohexane, bis-(4-hydroxycyclohexyl)-methane, 2,2-bis-(4-hydroxycyclohexyl)-propane or 1,1-bis-(hydroxymethyl)-cyclohex-3-ene, or they have aromatic nuclei, such as N,N-bis-(2-hydroxyethyl)-aniline or p,p'-bis-(2-hydroxyethylamino)-diphenylmethane.

The epoxide compounds can also be derived from mononuclear phenols, for example from resorcinol or hydroquinone; or they are based on polynuclear phenols, for example bis-(4-hydroxyphenyl)-methane, 4,4'-dihydroxybiphenyl, bis-(4-hydroxyphenyl)-sulfone, 1,1,2,2-tetrakis-(4-hydroxyphenyl)-ethane, 2,2,-bis-(4-hydroxyphenyl)-propane, 2,2-bis-(3,5-dibromo-4-hydroxyphenyl)-propane and novolaks which can be obtained by subjecting aldehydes, for example formaldehyde, acetaldehyde, chloral or furfuraldehyde, to a condensation reaction with phenols, such as phenol, or with phenols substituted in the nucleus by chlorine atoms or $C_1$–$C_9$alkyl groups, for example 4-chlorophenol, 2-methylphenol or 4-tert-butylphenol, or novolaks which can be obtained by a condensation reaction with bisphenols, as described above.

(III) Poly-(N-glycidyl) compounds which can be obtained, for example, by dehydrochlorinating the reaction products of epichlorohydrin with amines containing at least two amino hydrogen atoms. Examples of these amines are aniline, n-butylamine, bis-(4-aminophenyl)-methane, m-xylylenediamine or bis-(4-methylaminophenyl)-methane.

The poly-(N-glycidyl) compounds also include, however, triglycidyl isocyanurate, N,N'-diglycidyl derivatives of cycloalkyleneureas, such as ethyleneurea or 1,3-propyleneurea, and N,N'-diglycidyl derivatives of hydantoins, such as of 5,5-dimethylhydantoin.

(IV) Examples of poly-(S-glycidyl) compounds are di-S-glycidyl derivatives derived from dithiols, for example ethane-1,2-dithiol or bis-(4-mercaptomethylphenyl) ether.

(V) Examples of cycloaliphatic epoxide resins are bis-(2,3-epoxycyclopentyl) ether, 2,3-epoxycyclopentyl glycidyl ether or 1,2-bis-(2,3-epoxycyclopentyloxy)-ethane.

It is also possible, however, to use epoxide resins in which the 1,2-epoxide groups are attached to various heteroatoms or functional groups; these compounds include, for example, the N,N,O-triglycidyl derivative of 4-aminophenol, the glycidyl ether/glycidyl ester of salicylic acid, N-glycidyl-N'-(2-glycidyloxypropyl)-5,5-dimethylhydantoin or 2-glycidyloxy-1,3-bis-(5,5-dimethyl-1-glycidylhydantoin-3-yl)-propane.

Suitable epoxide curing agents (b) are acid, basic or catalytic curing agents. These include, for example, amines or amides, such as aliphatic, cycloaliphatic or aromatic, primary, secondary or tertiary amines, for example hexamethylenediamine, N,N-diethylpropylenediamine, bis-(4-aminocyclohexyl)-methane, 3,5,5-trimethyl-3-(aminomethyl)-cyclohexylamine ("isophoronediamine"), 2,4,6-tris-(dimethylaminomethyl)-phenol, p-phenylenediamine or bis-(4-aminophenyl)-methane; or polyamides, for example those formed from aliphatic polyamines and dimerized or trimerized unsaturated fatty acids; or polyhydric phenols, for example resorcinol, 2,2-bis-(4-hydroxyphenyl)-propane or phenol/formaldehyde resins (phenolnovolaks); or boron trifluoride and its complexes with organic compounds, for example $BF_3$-ether complexes or $BF_3$-amine complexes; or polybasic carboxylic acids and anhydrides thereof, for example, phthalic anhydride, tetrahydrophthalic anhydride or hexahydrophthalic anhydride or the corresponding acids.

Curing accelerators (c) can also be employed in the curing reaction; examples of such accelerators are tertiary amines or salts or quaternary ammonium compounds thereof, for example benzyldimethylamine, 2,4,6-tris-(dimethylaminomethyl)-phenol, 1-methylimidazole, 2-ethyl-4-methylimidazole, 4-aminopyridine, tripentylammonium phenate or tetramethylammonium chloride; or alkali metal alcoholates, for example Na alcoholates of 2,4-dihydroxy-3-hydroxymethylpentane.

Curable mixtures of this type can also contain suitable plasticizers, such as dibutyl phthalate, dioctyl phthalate or tricresyl phosphate, or reactive diluents, such as phenyl or cresyl glycidyl ether, butanediol diglycidyl ether or hexahydrophthalic acid diglycidyl ester.

Finally, it is possible to add to the curable mixtures, in any phase prior to curing, diluents, fillers and reinforcing agents, for example coal tar, bitumen, textile fibres, glass fibres, asbestos fibres, boron fibres, carbon fibres, mineral silicates, mica, powdered quartz, hydrated aluminium oxide, bentonites, kaolin or silica aerogel, or metal powders, for example aluminium powder or iron powder, and also pigments and colorants, such as carbon black, oxide colours, titanium dioxide and others. It is also possible to add to the curable mixtures other customary additives, for example flame-retarding agents, such as antimony trioxide, thixotropic agents and flow control agents, such as silicones, waxes or stearates (which in some cases are also used as mould release agents).

The preparation of the curable mixtures according to the invention can be carried out in a customary manner by means of known mixing units (stirrers, kneaders, rollers, etc.).

The curable epoxide resin mixtures according to the invention are used, in particular, in the fields of surface protection, electrical engineering, laminating processes and the building industry. They can be used in a formulation adapted in each case to suit the particular end-use, in an unfilled or filled state, as coating agents, paints, such as sintered powder paints, compression moulding materials, dipping resins, casting resins, injection moulding formulations, impregnating resins, adhesives, tooling resins, laminating resins, sealing compositions, surface fillers, floor covering compositions and binders for mineral aggregates.

They can be used preferably as sintered powder paints, impregnating resins and laminating resins, especially as impregnating and laminating resins.

The curing of the copolymers, according to the invention, containing glycidyl groups is advantageously carried out within the temperature range from 50° C. to 300° C., preferably 80°–250° C.

Curing can also be carried out in a known manner in two or more stages, the first curing stage being carried out at a low temperature and the subsequent curing at a higher temperature.

Curing can, if desired, also be carried out in two stages, by initially discontinuing the curing reaction prematurely or carrying out the first stage at a rather low temperature, whereby a curable precondensate which is still meltable and/or soluble (the so-called "B-stage") is obtained from the epoxy component (a), the curing agent (b) and the, optionally present, accelerator (c). A precondensate of this type can be used, for example, for the preparation of "prepregs", compression moulding materials or sintered powders.

The term "curing", as used here, denotes the conversion of the soluble, either liquid or meltable, polyepoxides into solid, insoluble and infusible, three-dimensionally crosslinked products or materials, as a rule with simultaneous shaping to give moulded articles, such as castings, mouldings and laminates, or impregnations, coatings, paint films and adhesive bonds.

The following examples illustrate the invention in greater detail.

PREPARATION EXAMPLES

Preparation of the so-called advanced epoxide resins

EXAMPLE 1

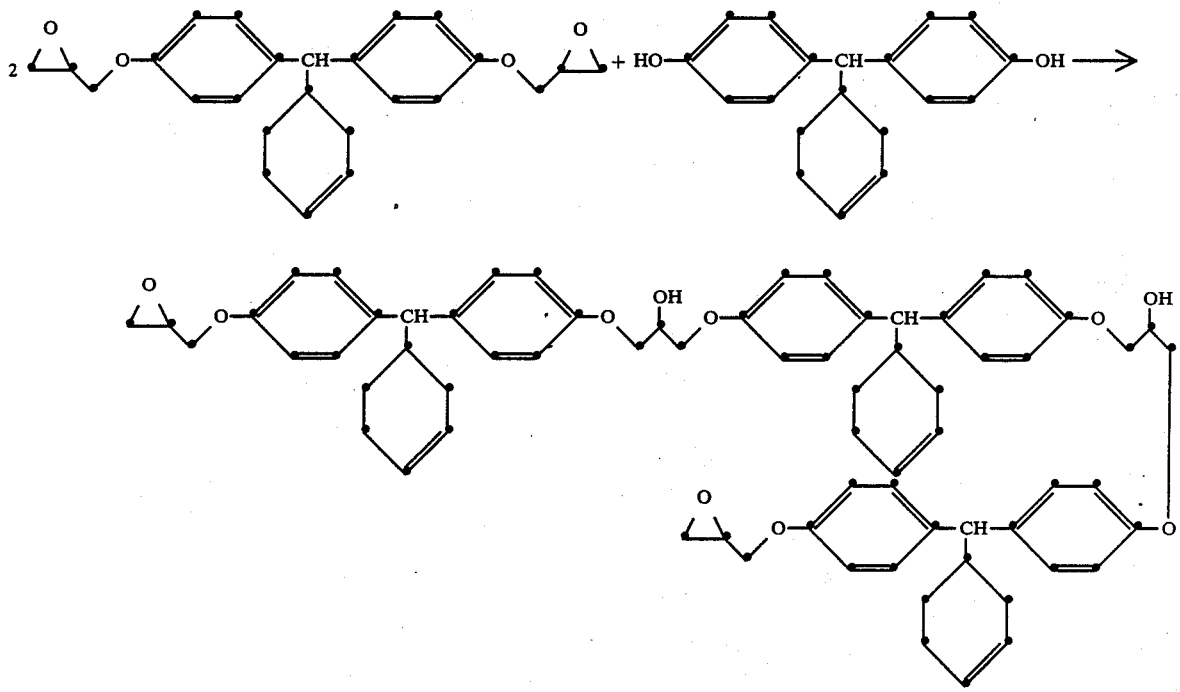

502.60 g (1.20 mol) of the diglycidyl ether of 4,4'-(cyclohex-3-en-1-yl-methylene)-diphenol (4.78 g equivalents/kg) and 0.31 g of 2-phenylimidazole are initially placed in a 750 ml sulfonation flask equipped with an anchor stirrer, a reflux condenser and a dropping funnel, and are heated to an internal temperature of 150° C. 168.22 g (0.60 mol) of 4,4'-(cyclohex-3-en-1-ylmethylene)-diphenol are added in portions, with stirring, in the course of approx. 1 hours, the temperature being kept below 170° C. Stirring is continued for a further 2 hours at 150°–160° C., the hot melt is poured onto a metal sheet and cooled to room temperature, and the solidified resin is pulverized. This gives 632 g of a slightly coloured solid resin.

Elementary analysis: calculated (%): C 77.79; H 7.19. found (%): C 76.99; H 7.21.

Epoxide value: calculated: 1.88 equivalents/kg. found: 1.47 equivalents/kg.

GPC (polystyrene standards): 4 main peaks; $M_w = 2590$; $M_n = 1227$.

EXAMPLE 2

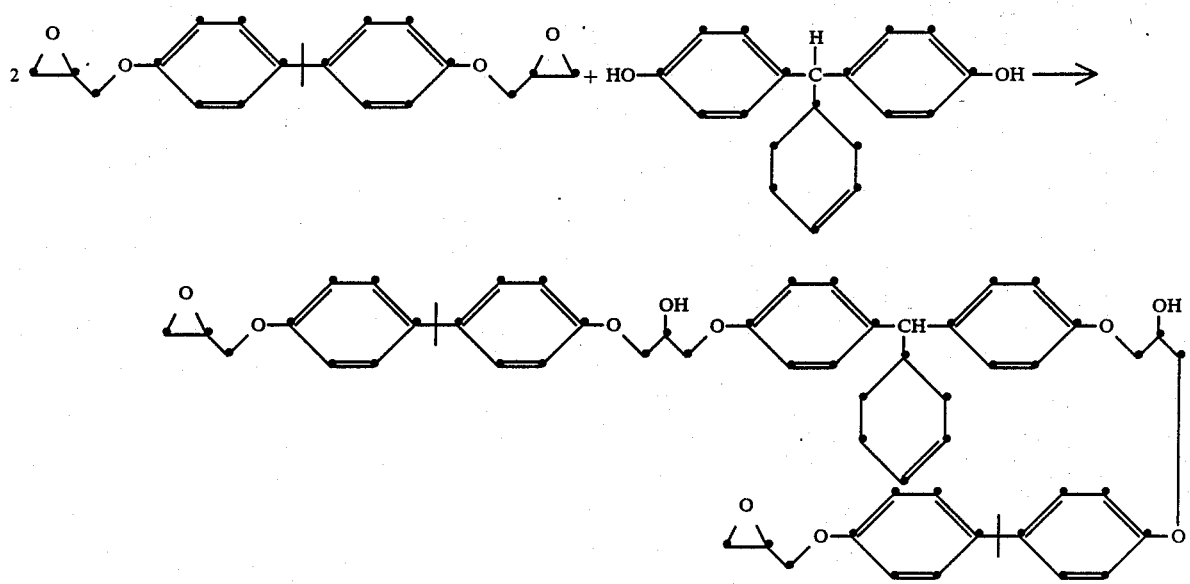

416.80 g (1.20 mol) of bisphenol A diglycidyl ether, 168.21 g (0.60 mol) of 4,4'-(cyclohex-3-en-1-ylmethylene)-diphenol and 0.48 g of 2-phenylimidazole are reacted in a 750 ml sulfonation flask by the process of Example 1. 561 g of a slightly coloured solid resin are obtained.

Elementary analysis: calculated (%): C 76.22; H 7.13. found (%): C 75.88; H 7.11.

Epoxide value: calculated: 2.08 equivalents/kg. found: 1.79 equivalents/kg.

GPC (polystyrene standards): 4 main peaks; $\overline{M}_w=4178$; $\overline{M}_n=1354$.

EXAMPLE 3

Epoxidation of the product from Example 2

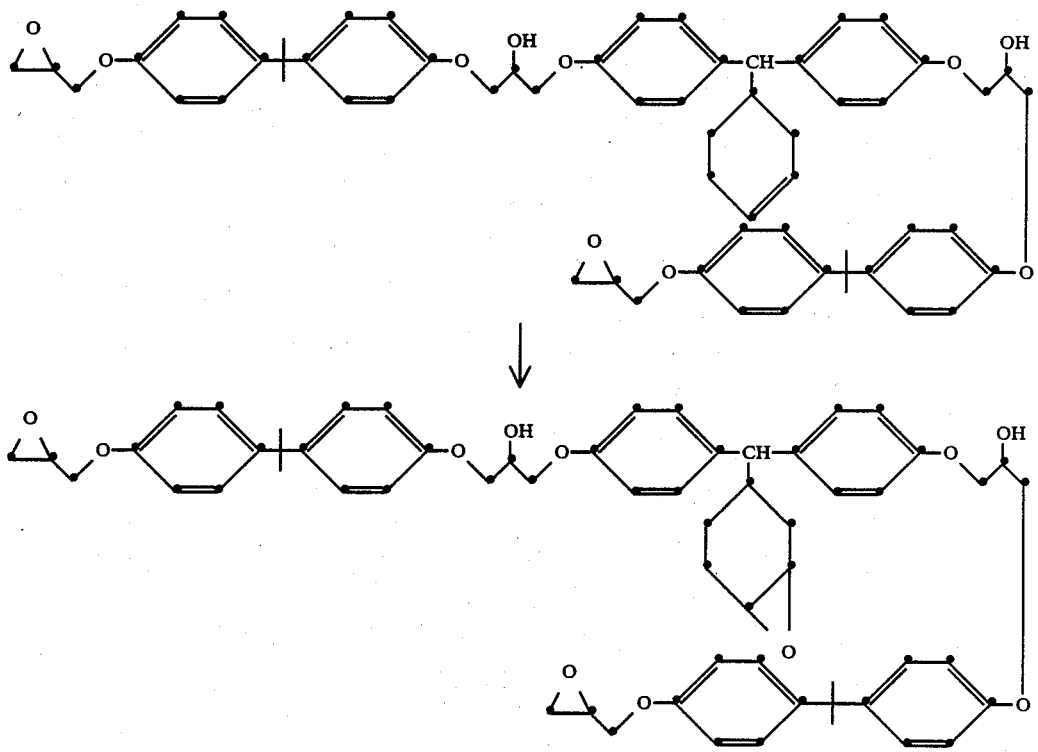

528.66 g (0.55 mol) of the product from Example 2 in 2.0 l of chloroform are initially placed in a 4.0 l sulfonation flask equipped with a thermometer, a stirrer, a cooler and an Impulsomat or Dosimat. 159.60 g (0.842 mol) of 40% peracetic acid are added dropwise at 35°–37° C. in the course of 1½ hours, the pH being kept constant (pH 4.0) with 20% NaOH. When the dropwise addition is complete, the reaction mixture is allowed to stand for approx. 4 hours more, to complete the reaction, and is then diluted with approx. 500 ml of chloroform, washed until neutral with 1 l of 1N NaOH and 3×1 l of water, dried over Na₂SO₄ and Na₂SO₃ and concentrated. Concentration and complete drying give 487.62 g (90.73% of theory) of a yellowish powder having an epoxide content of 2.59 equivalents/kg (84% of theory).

drying give 434.4 g of a yellowish powder having an epoxide content of 3.34 equivalents/kg (74.39% of theory).

EXAMPLE 5

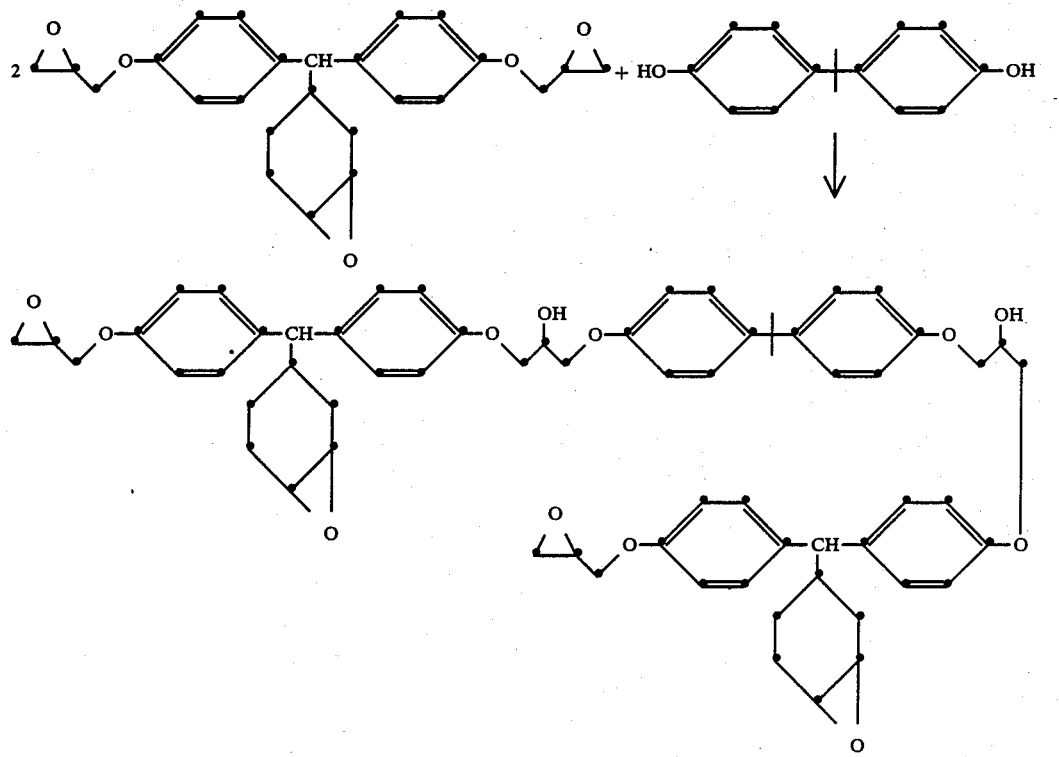

EXAMPLE 4

Epoxidation of the product from Example 1

585.97 g (0.55 mol) of the product from Example 1 and 1,200 ml of chloroform are initially placed in a 2.5 l sulfonation flask and are warmed to 45°–50° C. 478.50 g (2.53 mol) of 40% peracetic acid are then added dropwise at 45°–50° C. in the course of 5 hours, with the pH controlled to a value of 4.0. When the dropwise addition is complete, the reaction mixture is allowed to stand for approx. 2 hours more, to complete the reaction, and is then diluted with approx. 500 ml of chloroform, washed with 1 l of 1N NaOH and also with several times 1 l H₂O, dried over Na₂SO₄, freed from peroxides with Na₂SO₃, filtered and concentrated. Concentration under a high vacuum (approx. 13 Pa) and 47.17 g (0.10 mol) of the diglycidyl ether of 4,4'-(3,4-epoxycyclohexl-ylmethylene)-diphenol (epoxide group content=6.37 equivalents/kg), 11.42 g (0.05 mol) of bisphenol A and 0.04 g of 2-phenylimidazole are heated to an internal temperature of 150°–160° C. in a 100 ml sulfonation flask equipped with an anchor stirrer, a thermometer and a reflux condenser, and are kept at this temperature for 2½ hours, with stirring. The clear yellowish melt is poured onto a metal sheet and pulverized after it has solidified. 56.0 g of a slightly yellowish solid resin are obtained.

Elementary analysis: calculated (%): C 74.69; H 6.94. found (%): C 72.39; H 6.89.

Epoxide group content: calculated: 3.41 equivalents/kg; found: 2.94 equivalents/kg (86% of theory).

GPC (polystyrene standards): $\overline{M}_w=6113$; $\overline{M}_n=1351$.

EXAMPLE 6

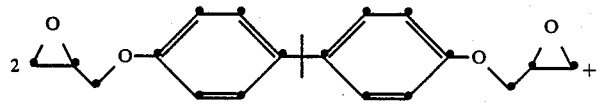

-continued

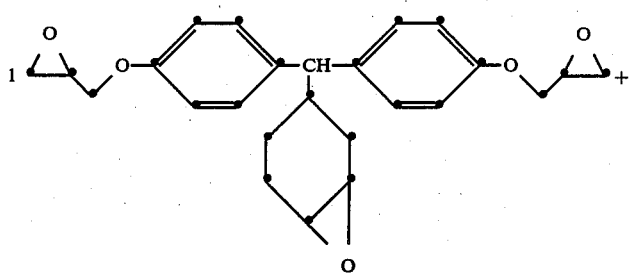

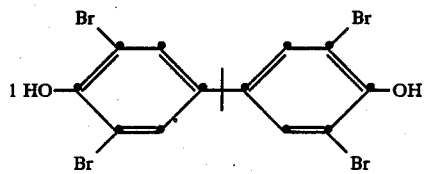

30.80 g of tetrabromobisphenol A (hydroxyl group content=3.68 equivalents/kg), 42.50 g of bisphenol A diglycidyl ether (epoxide group content=5.34 equivalents/kg), 26.70 g of the diglycidyl ether of 4,4'-(3,4-epoxycyclohex-1-ylmethylene)-diphenol (epoxide group content=6.37 equivalents/kg) and 0.08 g of 2-phenylimidazole are heated to an internal temperature of 160° C. in a 250 ml sulfonation flask equipped with an anchor stirrer, a thermometer, a reflux condenser and blanketing with $N_2$ inert gas, and are kept at this temperature for 6½ hours, with stirring. The clear, yellowish melt is poured onto a metal sheet and is pulverized after it has solidified. 93.96 g of a yellowish solid resin are obtained.

Epoxide group content: calculated: 2.84 equivalents/kg; found: 2.38 equivalents/kg (83% of theory).

GPC (polystyrene standards): $\overline{M}_w=2258$; $\overline{M}_n=932$.

Preparation of the intermediates for the so-called advancement reaction

EXAMPLE A

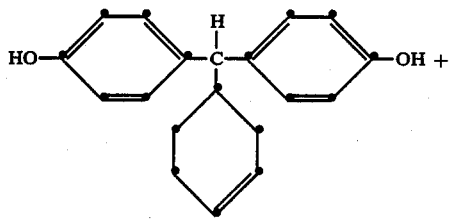

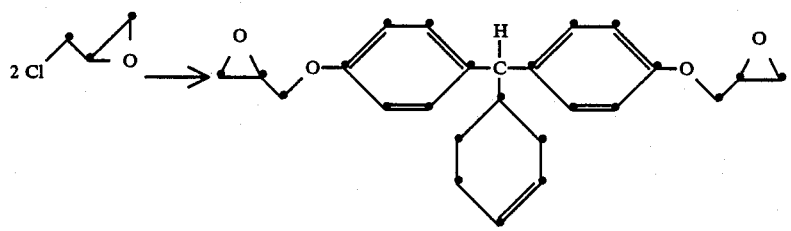

280.40 g (1.0 mol) of 4,4'-(cyclohex-3-en-1-ylmethylene)-diphenol, 1,110.40 g (12.0 mol) of epichlorohydrin and 150.00 g of isopropanol are initially placed in a 2.5 l sulfonation flask equipped with a stirrer, a reflux condenser, a thermometer and a dropping funnel, and are heated to an internal temperature of 70° C., with stirring. 224.00 g (2.80 mol) of 50% NaOH solution are added dropwise in the course of approx. 2 hours, the temperature being kept at 70°-75° C. Stirring is continued for a further 2 hours at 70° C. after the addition, the mixture is coded to 20° C. and the reaction product (a somewhat smeary suspension) is washed with twice 750 ml of 5% $NaHSO_4$ solution and once with 1,000 ml of water. The organic phase is dried over sodium sulfate, filtered and evaporated in vacuo. 368.9 g of a clear, slightly coloured resin are obtained after drying in vacuo at 120° C./1.3 Pa (3 hours).

Elementary analysis: calculated (%): C 76.50; H 7.19. found (%): C 75.67; H 7.24.

Epoxide value: calculated: 5.1 equivalents/kg. found: 4.7 equivalents/kg.

EXAMPLE B

Epoxidation of the product from Example a

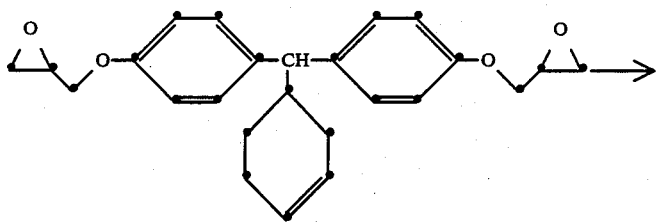

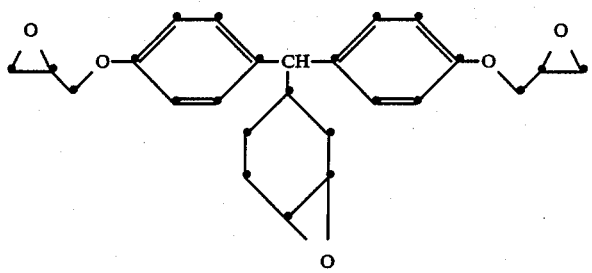

333.63 g (0.850 mol) of the diglycidyl ether from Example a, of epoxide content 4.305 equivalents/kg, are initially placed, together with 680 ml of chloroform, in a 2.5 l sulfonation flask equipped with a stirrer, a thermometer, a condenser, a pH meter, a pH electrode, a Dosimat and an Impulsomat. 246.50 g (1.292 mol) of 40% peracetic acid are added dropwise in the course of 4 hours at a temperature of 40°–50° C., the pH being kept constant throughout at a value of 4.0. When the dropwise addition is complete, the reaction mixture is allowed to react for a further hour and the aqueous phase is then separated off and the organic phase is neutralized with 2×500 ml of water and 1×250 ml of NaHCO$_3$, dried over Na$_2$SO$_4$ and freed from peroxides with Na$_2$SO$_3$, filtered and concentrated in vacuo (50°–70° C./665–1330 Pa).

Drying leaves 316.0 g (91.01% of theory) of a colorless powder having an epoxide content of 6.36 equivalents/kg and a viscosity of 5,835 mPas at 80° C. M$_n$/Mw=428/449.

IR (film): 3,500–3,200, 3,000–2,800, 1,600, 1,520, 1,240, 1,040 and 820 cm$^{-1}$. NMR (CDCl$_3$): 0.8–2.5 m 9H (cyclohexyl-H), 2.5–4.0 m 11H (glycidyl H2 methine-H), 6.8–7.2 d×d 8H (aromatic H).

Preparation of cyclohex-3-en-1-ylmethylenediphenol

EXAMPLE A

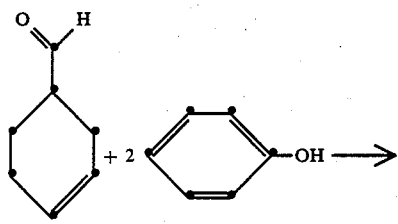

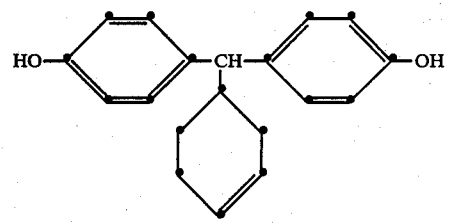

1,129.3 g (12.0 mol) of phenol, 10.0 ml of 3-mercaptopropionic acid, 76.0 g (0.40 mol) of toluene-4-sulfonic acid monohydrate and 600.0 ml of toluene are initially placed, under inert gas blanketing, in a 4 l sulfonation flask, equipped with a stirrer, a reflux condenser, a dropping funnel and a thermometer, and are stirred to form a solution. This is cooled to an internal temperature of +15° C. by means of an ice bath, and 220.2 g (2.0 mol) of 1,2,5,6-tetrahydrobenzaldehyde are added dropwise in the course of 1 hour, with such cooling that the internal temperature remains at approx. +15° C. The cooling bath is removed and the mixture is stirred for a further 6 hours at room temperature. The resulting suspension is filtered, and the residue on the filter is dried in vacuo at 80° C.

424.8 g (yield=75.7%, calculated on tetrahydrobenzaldehyde employed) of reddish-colored cyclohexenylmethylenediphenol are obtained. 319.6 g of colorless product are left after recrystallization from 1,300 ml of isopropanol (57% yield, relative to tetrahydrobenzaldehyde).

Melting point: 215°–216°

Elementary analysis (recrystallized product): calculated (%): C 81.40; H 7.19. found (%): C 81.02; H 7.21.

Application examples

I. Phenolic curing (by means of cresol novolak)

The following formulations are used, as 65% solutions in DMF, to coat aluminium sheets, which are then dried. The films thus obtained have a dry film thickness of approx. 50 μm. The glass transition temperature and the resistance to chemicals are determined after curing for 1 hour at 180° C.

| Test | A | B | C |
|---|---|---|---|
| Formulation | Product according to Example 4 100 parts (1) Novolak 31 parts (2) EMI-2,4 1.4 parts | Product according to Example 3 100 parts Novolak 44 parts EMI-2,4 2.0 parts | Product according to Example 5 100 parts Novolak 35 parts EMI-2,4 1.6 parts |
| Solution in DMF | 65% | 65% | 65% |
| Curing | 1 hour at 180° C. | 1 hour at 180° C. | 1 hour at 180° C. |
| (3)$T_G$ | 174° C. | 185° C. | 170° C. |
| (4)Rubbing test (20x) acetone | 0 | 0 | 0 |
| (5)Resistance to chemicals: | | | |
| 5N NaOH | 0 | 0 | 0 |
| 5N $H_2SO_4$ | 0 | 0 | 0 |

As can be seen from the above Table, the cured resins exhibits high glass transition temperatures and an excellent resistance to chemicals.

(1)Cresol novolak, hydroxyl group content = 8.3 equivalents/kg
(2)2-Ethyl-4-methylimidazole
(3)Glass transition temperature obtained by thermomechanical analysis.
(4)Acetone rubbing test: 0–5 0 = film not attacked 5 = film dissolved away
(5)Resistance to chemicals: the effect of 1 drop on the film for 1 hour (at room temperature), followed by scratching with spatula 0–5 0 = film not attacked 5 = film dissolved away
Notes:
(1)Uralac ® P 3400 is a solid, acid, saturated polyester made by Scado.
(2)A formulated accelerator based on a saturated, carboxyl-terminated polyester and $C_{12}$–$C_{16}$alkyl-trimethylammonium bromide.

II. Powder paint

Preparation of samples: the components of the formulation shown in the following table are ground and thoroughly mixed. The powder is applied to a preheated aluminium panel (180° C.) so as to produce a film thickness of 40–60 μm. The film is cured for 30 minutes at 180° C., and the properties listed in the table are then determined.

As can be seen, the cured resins give coatings free from yellowing and having good mechanical properties and good reesistance to chemicals. The high reactivity of the resin mixture, which is reflected in a short gel time, is remarkable.

TABLE

| Test | D | E | F |
|---|---|---|---|
| Formulation | Product according to Example 4 145 parts Uralac 3400(1) 855 parts Accelerator(2) 20 parts | Product according to Example 3 195 parts Uralac 3400(1) 805 parts Accelerator(2) 20 parts | Product according to Example 5 175 parts Uralac 3400(1) 825 parts Accelerator(2) 20 parts |
| Gel time at 180° C. (minutes) | 2 | 2 | 2 |
| Curing (°C.) | 180 | 180 | 180 |
| (minutes) | 30 | 30 | 30 |
| Yellowing | colourless | colourless | colourless |
| Erichsen impact indentation (cm.kg) | <10 | >180 | >180 |
| Erichsen indentation (mm) | <1 | >10 | >10 |
| Adhesion (0–5) (cross-cut test) | Gt 0 | Gt 0 | Gt 0 |
| Acetone test (0–5) (1 minute) | 3–4 | 2–3 | 2–3 |
| Konig hardness (seconds) | 208 | 218 | 216 |
| $T_g$ (°C.) (DSG) | 84 | 85 | 88 |
| Differential thermogravimetry; 10° C./minute | | | |
| T(−5%) (°C.) | 370 | 370 | 365 |
| T(−10%) (°C.) | 395 | 390 | 390 |
| T(−50%) (°C.) | 460 | 450 | 460 |

III. Laminate (printed circuit board)

A 75% solution of the product from Example 6 in methyl ethyl ketone is prepared and is used to formulate an impregnating solution of the following composition.
133.0 parts of 75% solution of the product from Example 6,
37.7 parts of 10% solution of dicyandiamide in methylglycol,
3.9 parts of 5% solution of benzylmethylamine in methylglycol and
29.0 parts of methylglycol.

A glass fabric (type 7628 CS, finish Z 6040) is impregnated with this solution and is dried in a circulating air oven at 170° C. for 4½ minutes. The prepregs are then compressed, together with copper foil, for 2 hours at 170° C., using a pressure of 20–40 kg/cm², to give laminates having the following properties.

| | |
|---|---|
| Glass transition temperature $T_G$ (DSG): | 160° C. |
| Absorption of N—methylpyrrolidone: | 0.0% |
| Pressure cooker test (1 hour): | successful |
| Flammability (UL-94): | V-O |

What is claimed is:

1. A process for curing a curable epoxide resin which comprises:

incorporating into the curable epoxide resin a compound of formula VIII

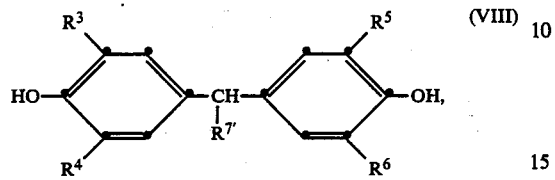

in which $R^3$, $R^4$, $R^5$ and $R^6$ independently of one another are hydrogen, $C_1$–$C_6$-alkyl, chlorine or bromine, and $R^{7'}$ is a radical of formula III, IV, V or VI

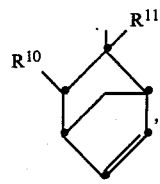

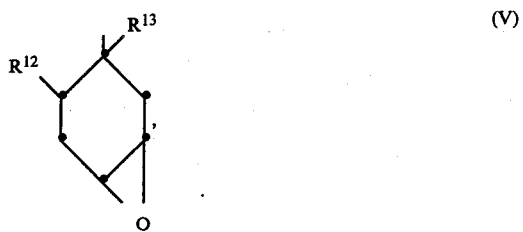

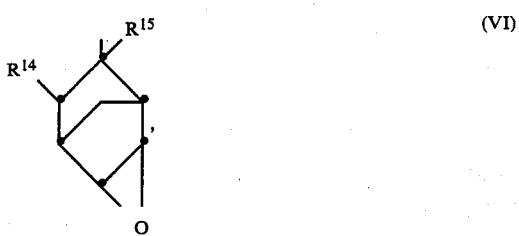

where $R^8$, $R^{10}$, $R^{12}$ and $R^{14}$ are hydrogen, $C_1$–$C_6$-alkyl or phenyl, and $R^9$, $R^{11}$, $R^{13}$ and $R^{15}$ are hydrogen or $C_1$–$C_6$-alkyl, and subsequently curing the mixture at 50° C. to 300° C.

* * * * *